United States Patent [19]

Warriner

[11] Plant 5,037

[45] Apr. 12, 1983

[54] ROSE PLANT—71-4992

[75] Inventor: William A. Warriner, Tustin, Calif.

[73] Assignee: Jackson & Perkins Company, Medford, Oreg.

[21] Appl. No.: 318,998

[22] Filed: Nov. 6, 1981

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Whinston & Dellett

[57] ABSTRACT

Rose plant of hybrid tea class characterized by vigorous, upright plant, open blooms in all weather, quilled, deltoid shaped petals, red color of blossom and little fragrance.

1 Drawing Figure

This present invention relates to a new and distinct variety of rose plant of the hybrid tea class which was originated by me by crossing an unnamed variety with another unnamed variety, the male (pollen) parent, 64-16181, being also the pollen parent of rose American Pride, U.S. Plant Pat. No. 4,139.

The primary objective of this breeding was to produce a new rose variety combining the plant habit of the pollen parent with the slightly lighter color and better opening characteristic of the seed parent, seedling No. 67-9016. This objective was substantially achieved along with other desirable improvements as evidenced by the following unique combination of characteristics which are outstanding in the new variety and which distinguish it from its parents as well as from all other varieties of which I am aware:

1. A plant similar in growth habit to the variety, American Pride, U.S. Plant Pat. No. 4,139, but with numerous differences in characteristics.
2. Flower opening habit in spring weather different than that of American Pride in that flowers open faster with little or no "balling" (failure to open).
3. Petal edges tend to curl more than those of American Pride giving a pointed look to the flower.
4. Petals of this new variety more deltoid in shape compared to a round petal of American Pride.
5. Bud and opening color slightly lighter red than color of American Pride.
6. Very little or no fragrance.
7. Peduncles and upper stems slightly weaker than those of American Pride.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown at Irvine, Calif., in August.

Blooming habit: Continuous.

Bud:

*Size.*—3 cm when petals start to unfurl.

*Form.*—Pointed ovoid.

*Color.*—When sepals first divide, Red 53B except where first exposed to sunlight 53A; when half blown, upper side of petals Red 53B; lower side of petals 53C.

*Sepals.*—Color: Outer surface Green 138A, smooth; three appendaged sepals lightly appendaged; two unappendaged sepals, hairy edge.

*Receptacle.*—Color: Green 138A. Shape: Funnel. Size: Long, small. Surface: Smooth.

*Peduncle.*—Length: Short. Surface: Smooth, slightly prickly on some stems. Color: Medium green to bronzy. Strength: Stiff, sometimes bending.

*Opening.*—Spiral type.

Bloom:

*Size.*—Large. Average open size 10 to 12 cm.

*Borne.*—Mostly singly.

*Stems.*—Long, normal.

*Form.*—When first open, high center. Permanence: Outer petal edges slightly curled.

*Color.*—Center of flower: Upper side of petals Red 46B. Reverse side of petals Red 46C. Base of petals pale yellow to white area approximately 1 cm. long. General tonality from a distance Red 46A.

*Variegations.*—Occasional vegetative green streak in midribs of outer petals.

*Discoloration.*—General tonality at end of first day, none. Third day, little change.

*Fragrance.*—None.

Petals:

*Texture.*—Thick.

*Shape.*—Oval to deltoid.

*Form.*—Edges slightly quilled.

*Arrangement.*—Imbricated. Petaloids in center, few.

*Persistence.*—Drop off cleanly.

*Lastingness.*—On the plant, long. As cut flowers, long.

Reproductive parts:

*Anthers.*—Medium, many. Color: Yellow. Arrangement: Regular around styles.

*Filaments.*—Color: Nearly white.

*Pollen.*—Gold yellow.

*Styles.*—Color: Pale yellow to red near stigmas.

PLANT

Form: Bush.

Growth: Very vigorous, upright branching.

Foliage: Number of leaflets on normal mid-stem leaves: 5 or 7.

*Size.*—Medium.

*Quantity.*—Normal.

*Color.*—New foliage: Greyed Purple 183B. Old foliage: Green 131A.

Leaflets:

*Shape.*—Oval pointed.

*Texture.*—Upper side, leathery.

*Edge.*—Serrated.

*Serration.*—Single, small.

*Petiole.*—Rachis: Color, reddish. Underside: prickles.

*Stipules.*—Long.

*Disease resistance.*—Slightly susceptible, resistant to mildew under normal growing conditions at Irvine, Calif.

Wood:

*New wood.*—Color: Light green. Bark: Smooth

*Old wood.*—Color: Green. Bark: Smooth.

Prickles:

*Quantity.*—On main stalks from base, ordinary. On laterals from stalk, ordinary.

*Form.*—Long base, long hooked downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its vigorous, upright plant, ability to open blooms well in all weather, quilled petals, red color lighter than that of American Pride, deltoid shaped petals and little fragrance.

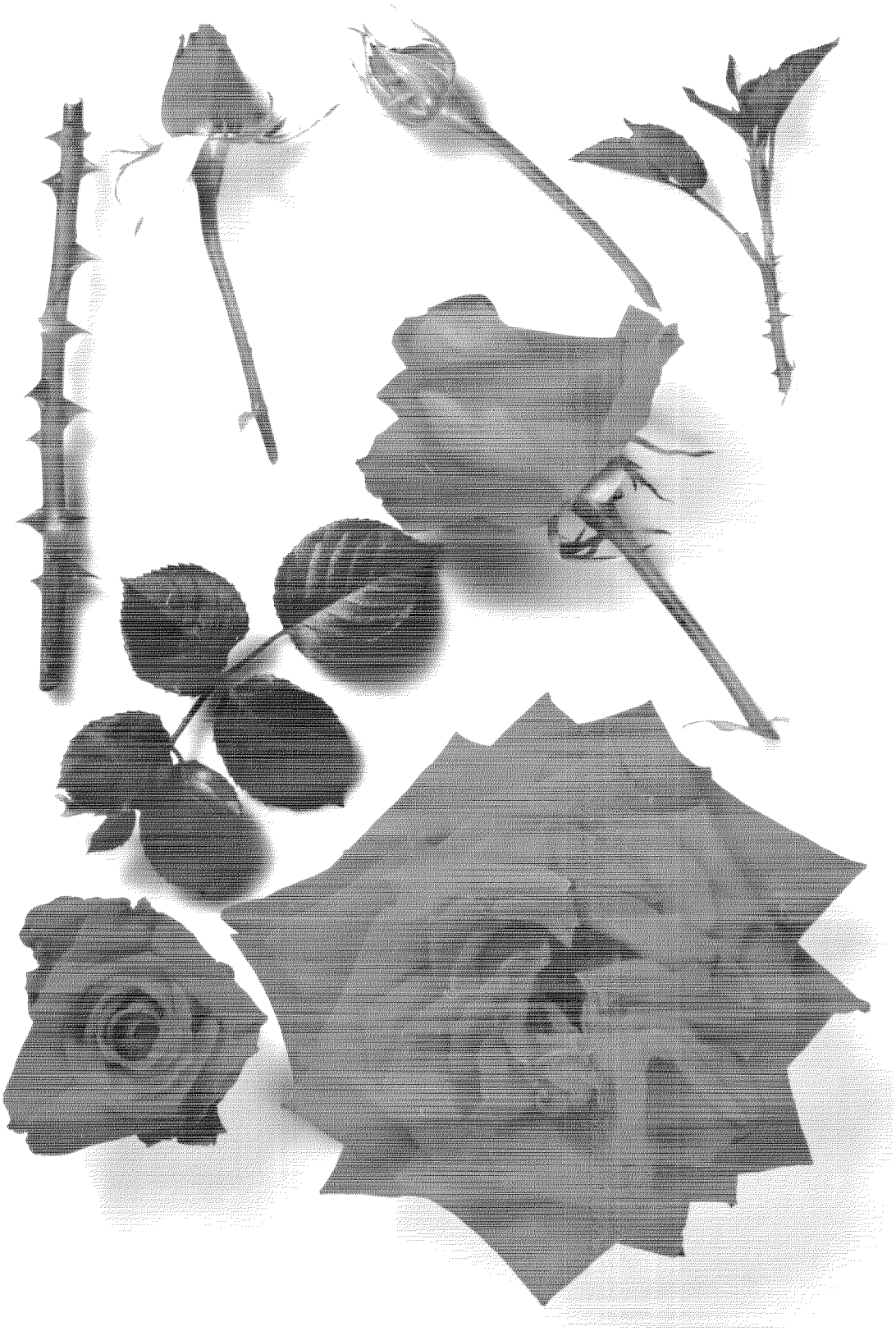

* * * * *